(12) United States Patent
Gao et al.

(10) Patent No.: US 6,919,334 B2
(45) Date of Patent: Jul. 19, 2005

(54) ANTIDEPRESSANT AZAHETEROCYCLYMETHYL DERIVATIVES OF 4,5-DIHYDROIMIDAZO[1,4,5-DE][1,4] BENZOXAZINE

(75) Inventors: Hong Gao, Belle Mead, NJ (US); Gary Paul Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/659,531

(22) Filed: Sep. 10, 2003

(65) Prior Publication Data

US 2004/0127493 A1 Jul. 1, 2004

Related U.S. Application Data

(60) Provisional application No. 60/410,074, filed on Sep. 12, 2002.

(51) Int. Cl.[7] .................. C07D 498/14; A61K 31/5365; A61P 25/24; A61P 3/04; A61P 25/32
(52) U.S. Cl. ..................................... 514/230.2; 544/101
(58) Field of Search ........................ 544/101; 514/230.2

(56) References Cited

FOREIGN PATENT DOCUMENTS

WO    WO 94/01437 A1    1/1994

OTHER PUBLICATIONS

Bundgaard, H. (ed.), *Design of Prodrugs*, Elsevier (1985), Ch. 1 (pp. 1–92), Ch. 4 (pp. 157–176), Ch. 5 (pp. 177–198), and Ch. 6 (pp. 199–241).
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, 77(4):285–298 (1988).
Eliel, E. L., *Stereochemistry of Carbon Compounds*, McGraw Hill, NY (1962) Ch. 4, pp. 46–87.
Higuchi and Stella (eds.), *Prodrugs as Novel Drug Delivery Systems*, American Chemical Society (1975), pp. 1–115 and 196–223.
Jacques, J. et al., *Enantiomers, Racemates and Resolutions*, Wiley Interscience, NY (1981) pp. 251–434.
*Remington's Pharmaceutical Sciences*, 17th Ed., Gennaro, A. R. (Ed.), Mack Publishing Company, Easton, PA (1985) pp. 1409–1677.
Widder, et al. (ed.), *Methods in Enzymology*, vol. 112, Academic Press (1985), pp. 309–396.
Artigas, F., et al., "Pindolol induces a rapid improvement of depressed patients treated with serotonin reuptake inhibitors," *Arch Gen Psychiatry*, Mar. 1994, 51, 248–251.
Blier, P., et al., "Effectiveness of pindolol with selected antidepressant drugs in the treatment of major depression," *J. of Clinical Psychopharmacology*, 1995, 15(3), 217–222.
Bundgaard, H., "Means to enhance penetration; Prodrugs as a means to improve the delivery of peptide drugs," *Advanced Drug Deliver Reviews*, 1992, 8, 1–38.

Cheetham, S.C., et al., "[³H]paroxetine binding in a rat frontal cortex strongly correlates with [³H]5–HT uptake: effect of administration of various antidepressant treatments," *Neuropharmacol.*, 1993, 32(8), 737–743.
Hall, M.D., et al., "{³H}8–hydroxy–2–(Di–n–propylamino)tetralin binding to pre– and postsynaptic 5–hydroxytryptamine sites in various regions of the rat brain," *J. Neurochem.*, 1985, 44, 1685–1696.
Krogsgaard–Larsen, et al. (Eds.), "Design and Application of Prodrugs," *Texbook of Drug design and Development*, 1991, Chap. 5, 113–191.
Lazareno, S., "Pharmacological characterization of acetylcholine–stimulated [³S]–GTPγS binding mediated by human muscarinic m1–m4 receptors: antagonist studies," *Br. J. Pharmacol.*, 1993, 109, 1120–1127.
Perez, V., et al., "Randomised, double–blind, placebo–controlled trial of pindolol in combination with fluoxetine antidepressant treatment," *The Lancet*,m May 31, 1997, 349, 1594–1597.
Tome, M.B., et al., "Serotonergic autoreceptor blocade in the reduction of antidepressant latency: personality variables and response to paroxetine and pindolol," *J. Affect Disord*, 1997, 44, 101–109.
Tome, M.B., et al., "Paroxetine and pindolol: a randomized trial of serotonergic antoreceptor blockade in the reduction of antidepressant latency," *Int. Clin. Pyschopharmacol*, 1997, 12, 81–89.
Wilen, S.H., "Tables of Resolving Agents and Optical Resolutions," *Univ. of Notre Dame Press, Notre Dame, IN*, E.L. Eliel (Ed.), 1972, p. 268–298.
WIlen, S.H., et al., "Strategies in optical resolutions," *Tetrahedron*, 1977, 33, 2725–2736.

*Primary Examiner*—Mark L. Berch
*Assistant Examiner*—Kahsay Habte
(74) *Attorney, Agent, or Firm*—Woodcock Washburn LLP

(57) ABSTRACT

Compounds of the formula:

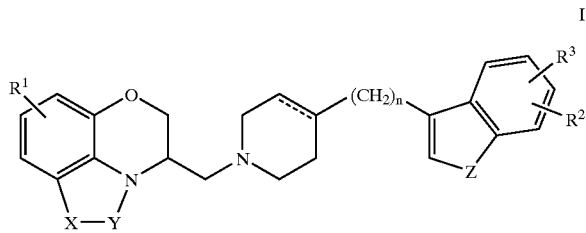

are useful for the treatment of depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder, social anxiety disorder, generalized anxiety disorder, obesity, eating disorders such as anorexia nervosa and bulimia nervosa, vasomotor flushing, cocaine and alcohol addiction, sexual dysfunction and related illnesses.

28 Claims, No Drawings

ANTIDEPRESSANT AZAHETEROCYCLYMETHYL DERIVATIVES OF 4,5-DIHYDROIMIDAZO[1,4,5-DE][1,4] BENZOXAZINE

CROSS-REFERENCE TO RELATED APPLICATIONS

This application claims the benefit of U.S. application Ser. No. 60/410,074, filed Sep. 12, 2002, the disclosure of which is incorporated herein by reference in its entirety.

FIELD OF THE INVENTION

This invention relates to antidepressant azaheterocyclyl-methyl derivatives of 4,5-dihydroimidazo[1,4,5-de][1,4] benzoxazine, to processes for preparing them, methods of using them and to pharmaceutical compositions containing them.

BACKGROUND OF THE INVENTION

Major depression is a serious health problem affecting more than 5% of the population, with a lifetime prevalence of 15–20%.

Selective serotonin reuptake inhibitors have produced success in treating depression and related illnesses and have become among the most prescribed drugs. They nonetheless have a slow onset of action, often taking several weeks to produce their full therapeutic effect. Furthermore, they are effective in less than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DETAILED DESCRIPTION OF THE INVENTION

In accordance with this invention, there is provided a group of novel compounds of Formula I:

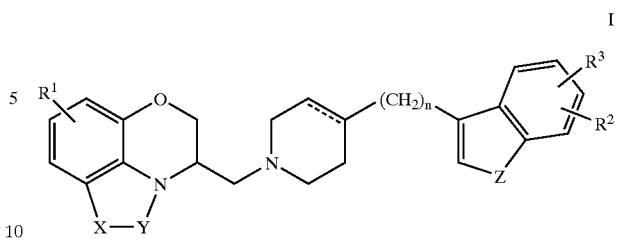

wherein
X—Y is —N=C($R^4$)—, —NH—C(O)—, —NH—C(O)—C(O)—, —NH—C(S)— or —NH—S(O)$_2$—;

Z is O, S or $NR^5$, in which $R^5$ is hydrogen or alkyl of 1 to 6 carbon atoms;

$R^1$, $R^2$ and $R^3$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyl of 2 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

$R^4$ is hydrogen, halo, amino, mono- or di-alkylamino in which each alkyl group has 1 to 6 carbon atoms or alkyl of 1 to 6 carbon atoms;

the dotted line represents an optional double bond; and n is 0, 1 or 2;

or a pharmaceutically acceptable salt thereof.

$R^1$ is preferably hydrogen, halo, cyano, trifluoromethyl, alkyl of 1 to 6 carbon atoms or alkoxy of 1 to 6 carbon atoms. More preferably, $R^1$ is hydrogen, halo or alkoxy of 1 to 6 carbon atoms. In still more preferred embodiments of the present invention, $R^1$ is hydrogen.

$R^2$ and $R^3$ are preferably independently selected from hydrogen, hydroxy, halo, cyano, carboxamido, alkyl of 1 to 6 carbon atoms, or alkoxy of 1 to 6 carbon atoms. In still more preferred embodiments of the present invention $R^2$ and $R^3$ are preferably independently selected from hydrogen, cyano or halogen.

$R^4$ is preferably hydrogen, amino or alkyl of 1 to 6 carbon atoms. More preferably, $R^4$ is hydrogen or alkyl of 1 to 3 carbon atoms.

Z is preferably $NR^5$. Preferably n is 0. The dotted line preferably represents a double bond.

$R^5$ is preferably hydrogen or alkyl of 1 to 3 carbon atoms. More preferably, $R^5$ is hydrogen or methyl.

In other preferred embodiments of the invention is provided compounds of Formula Ia.

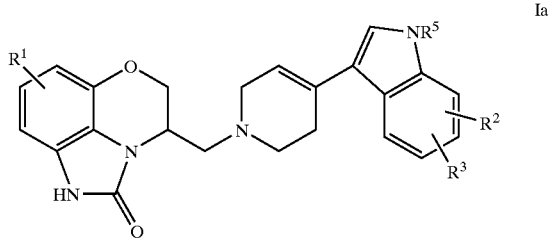

wherein $R^1$, $R^2$, $R^3$ and $R^5$ are as described above.

This invention relates to both the R and S stereoisomers of the 4-aminomethyl-4,5-dihydroimidazo[1,4,5-de][1,4]

benzoxazines as well as to mixtures of the R and S stereoisomers. Throughout this application, the name of the product of this invention, where the absolute configuration of the compounds of the invention is not indicated, is intended to embrace the individual R and S enantiomers as well as mixtures of the two. In some embodiments of the present invention the S enantiomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, New York, 1962); Wilen, S. H. *Tables of Resolving Agents and Optical Resolutions* p. 268 (E. L. Eliel, Ed., Univ. of Notre Dame Press, Notre Dame, Ind. 1972).

"Alkyl," as used herein, refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

"Alkanamido," as used herein, refers to the group R—C(=O)—NH— where R is an alkyl group of 1 to 5 carbon atoms.

"Alkanoyl," as used herein, refers to the group R—C(=O)— where R is an alkyl group of 1 to 5 carbon atoms.

"Alkanoyloxy," as used herein, refers to the group R—C(=O)—O— where R is an alkyl group of 1 to 5 carbon atoms.

"Alkanesulfonamido," as used herein, refers to the group R—S(O)$_2$—NH— where R is an alkyl group of 1 to 6 carbon atoms.

"Alkanesulfonyl," as used herein, refers to the group R—S(O)$_2$— where R is an alkyl group of 1 to 6 carbon atoms.

"Alkoxy," as used herein, refers to the group R—O— where R is an alkyl group of 1 to 6 carbon atoms.

"Carboxamido," as used herein, refers to the group NH$_2$—C(=O)—.

"Carboalkoxy," as used herein, refers to the group R—O—C(=O)— where R is an alkyl group of 1 to 5 carbon atoms.

"Halogen" (or "halo"), as used herein, refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:

4-{[4-(1 H-Indol-3-yl)-3,6-dihydropyridin-1(2H)-yl]methyl)-4,5-dihydroimidazo[1,5,4-de][1,4]benzoxazin-2(1H)-one;

4-{[4-(5-Fluoro-1H-indol-3-yl)-3,6-dihydropyridin-1(2H)-yl]methyl)-4,5-dihydroimidazo[1,5,4-de][1,4]benzoxazin-2(1H)-one;

4-{[4-(5-Chloro-1H-indol-3-yl)-3,6-dihydropyridin-1(2H)-yl]methyl)-4,5-dihydroimidazo[1,5,4-de][1,4]benzoxazin-2(1H)-one;

3-{1-[(2-Oxo-1,2,4,5-tetrahydroimidazo[1,5,4-de][1,4]benzoxazin-4-yl)methyl-1,2,3,6-tetrahydropyridin-4-yl}-1H-indole-5-carbonitrile;

4-{[4-(7-Fluoro-1H-indol-3-yl)-3,6-dihydropyridin-1(2H)-yl]methyl)-4,5-dihydroimidazo[1,5,4-de][1,4]benzoxazin-2(1H)-one;

4-{[4-(1H-indol-3-yl)-3,6-dihydropyridin-1(2H)-yl]methyl}-2-methyl-4,5-dihydroimidazo[1,5,4-de][1,4]benzoxazine;

Compounds of the present invention are prepared in accordance with the following general description and specific examples. Variables used are as defined for Formula I, unless otherwise noted. Specifically, compounds of the invention in which X—Y is —NH—(CO)— are prepared according to the process outlined in Scheme 1. The appropriately substituted 2-amino-3-nitrophenol (1) is alkylated with epibromohydrin, epichlorohydrin or a glycidyl arylsulfonate such as glycidyl tosylate or glycidyl nitrobenzenesulfonate in the presence of a suitable base such as potassium carbonate to give a glycidyl ether (2). Further treatment of the glycidyl ether with a base such as sodium hydride in a polar solvent such as N,N-dimethylformamide (DMF) causes cyclization to the nitrobenzoxazine methanol (3), which is converted to the tosylate (4) by treatment with p-toluenesulfonyl chloride (TsCl) in the presence of a tertiary base such as diisopropylethylamine and a catalyst such as 4-(dimethylamino)pyridine (DMAP). Following reduction of the nitro group to the amine (5) by treatment with hydrogen over a suitable catalyst such as 10% palladium on carbon, cyclization to the imidazolone (6) is effected by reaction with carbonyl diimidazole (CDI) in the presence of a tertiary base. Replacement of the tosylate with the appropriately substituted azaheterocycle in some high boiling solvent such as dimethyl sulfoxide gives the title compounds of the invention. Substitution of oxalyl diimidazole, thiocarbonyl diimidazole or sulfonyl diimidazole for carbonyl diimidazole in the cyclization reaction described above leads to compounds of the invention in which X—Y is —NH—C(O)—C(O)—, —NH—C(S)— or —NH—S(O)$_2$, respectively.

Scheme 1

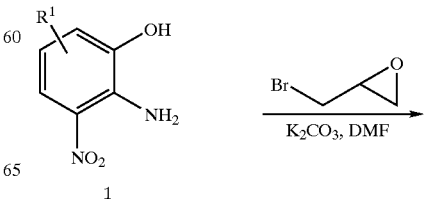

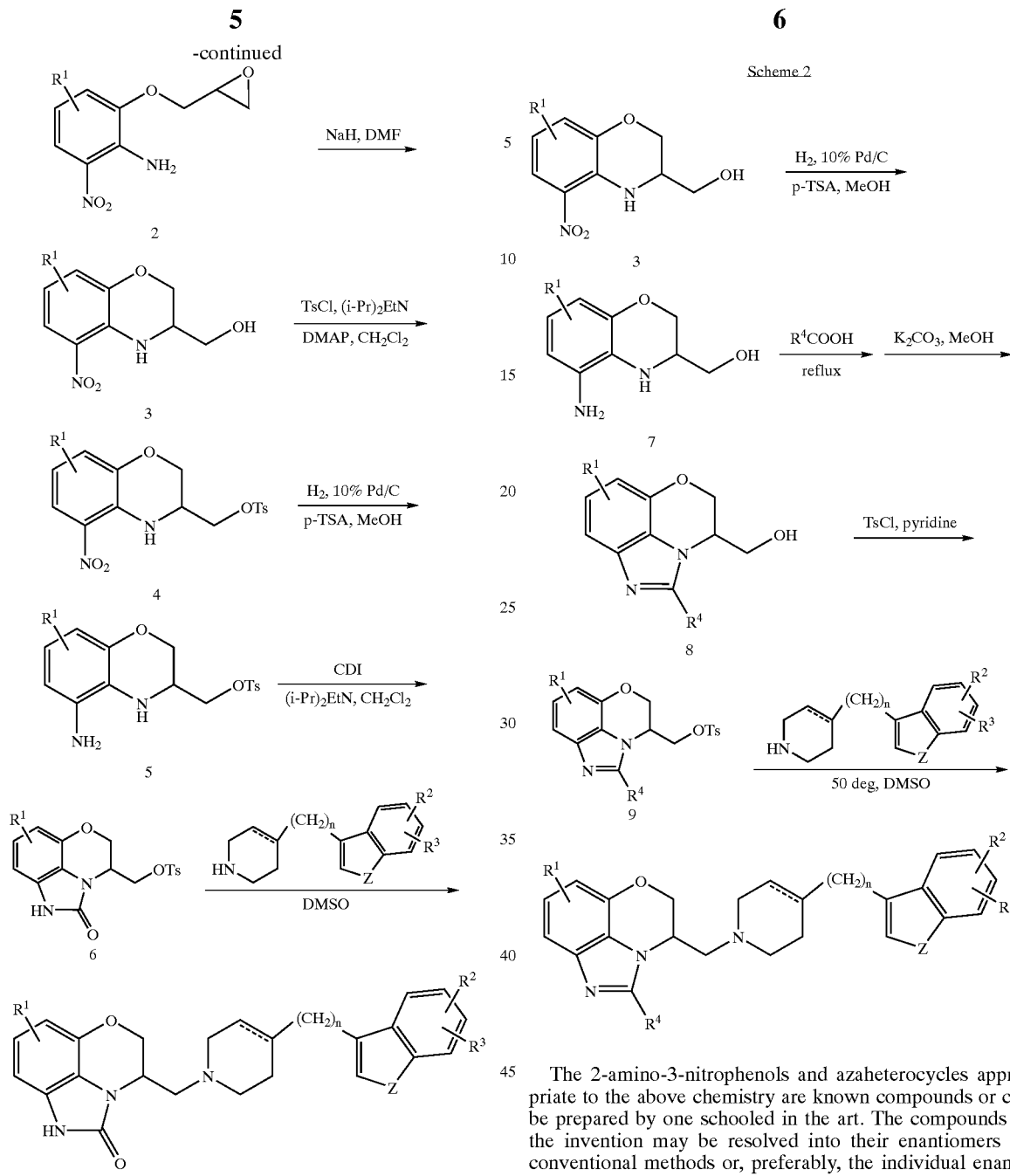

Compounds of the invention in which X—Y is —N=C(R⁴)— are prepared according to the method outlined in Scheme 2. Specifically, the nitrobenzoxazine (3) described above in Scheme 1 is reduced to the amine (7) by treatment with hydrogen over a suitable catalyst such as 10% palladium on carbon. Cyclization to the imidazole is effected by refluxing in the appropriately substituted carboxylic acid for several hours, a process which is accompanied by solvolysis of the alcohol to the corresponding carboxylic acid ester. Hydrolysis of the ester by treatment with potassium carbonate in methanol gives the tricyclic alcohol (8). Following conversion of the alcohol to the tosylate (9) by treatment with p-toluenesulfonyl chloride in pyridine, replacement of the tosylate with the appropriately substituted azaheterocycle in a high boiling solvent such as dimethyl sulfoxide gives the title compounds of the invention.

The 2-amino-3-nitrophenols and azaheterocycles appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzoxazine methanamine) or (2S)-(+)-glycidyl 3-nitrobenzenesulfonate or tosylate (for the R enantiomer) in place of epihalohydrin or racemic glycidyl tosylate in the procedures above.

A protocol similar to that used by Cheetham et al. (*Neuropharmacol.* 32:737, 1993) was used to determine the affinity of the compounds of the invention for the serotonin transporter. The compound's ability to displace ³H-paroxetine from male rat frontal cortical membranes was determined using a Tom Tech filtration device to separate bound from free ³H-paroxetine and a Wallac 1205 Beta Plate® counter to quantify bound radioactivity. $K_i$'s thus determined for standard clinical antidepressants are 1.96 nM for fluoxetine, 14.2 nM for imipramine and 67.6 nM for zimelidine. A strong correlation has been found between ³H-paroxetine binding in rat frontal cortex and ³H-serotonin uptake inhibition.

Affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following a modification of the procedure of Hall et al., *J. Neurochem.* 44, 1685 (1985), which utilizes CHO cells stably transfected with human 5-HT$_{1A}$ receptors. The 5-HT$_{1A}$ affinities for the compounds of the invention are reported below as percent displacement at 1 micromolar.

Antagonist activity at 5-HT$_{1A}$ receptors was established by using a $^{35}$S-GTPγS binding assay similar to that used by Lazareno and Birdsall (*Br. J. Pharmacol.* 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the I$_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity % @ 1 μM | 5-HT$_{1A}$ Function IC$_{50}$ (μM) (I$_{max}$) |
|---|---|---|---|
| Example 1 | 1.07 | 94 | 0.30 (30) |
| Example 2 | 2.08 | 36 | 0.30 (30) |
| Example 3 | 15.00 | 81 | 0.30 (30) |
| Example 4 | 3.55 | 49 | 0.75 (100) |
| Example 5 | 1.23 | 48 | 0.75 (100) |
| Example 6 | 1.86 | 39 | 0.45 (100) |

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorders (including but not limited to trichotillomania), obsessive compulsive spectrum disorders (including but not limited to autism), social anxiety disorder, generalized anxiety disorder, obesity, eating disorders such as anorexia nervosa and bulimia nervosa, vasomotor flushing, cocaine and alcohol addiction, sexual dysfunction (including but not limited to premature ejaculation), incontinence (including, but not limited to fecal incontinence, urge incontinence, overflow incontinence, passive incontinence, reflex incontinence, stress urinary incontinence urinary exertional incontinence and urinary incontinence), and pain (including, but not limited to migraine, chronic back pain, phantom limb pain, neuropathic pain such as diabetic neuropathy, and post herpetic neuropathy) and related illnesses. Moreover, the compounds of this invention have potent affinity for and antagonist activity at brain 5HT$_{1A}$ serotonin receptors. Recent clinical trials employing drug mixtures (e.g., fluoxetine and pindolol) have demonstrated a more rapid onset of antidepressant efficacy for a treatment combining SSRI activity and 5HT$_{1A}$ antagonism (Blier and Bergeron, 1995; F. Artigas et al., 1996; M. B. Tome et al., 1997). The compounds of the invention are thus exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions that are sterile solutions or suspensions can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I and Ia. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). *Design and Application of Prodrugs, Textbook of Drug Design and Development*, Chapter 5, 113–191 (1991), Bundgaard, et al., *Journal of Drug Deliver Reviews*, 8:1–38(1992), Bundgaard, *J. of Pharmaceutical Sciences*, 77:285 et seq. (1988); and Higuchi and Stella (eds.) *Prodrugs as Novel Drug Delivery Systems*, American Chemical Society (1975).

The following examples illustrate the production of representative compounds of this invention.

Intermediate 1

2-Nitro-6-oxiranylmethoxy-phenylamine

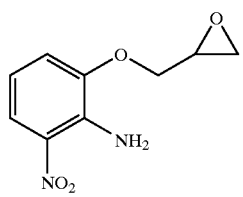

A solution of 2-amino-3-nitro-phenol (18.0 g, 0.117 mol) and epibromohydrin (21.0 g, 0.15 mol) in DMF (200 mL) containing potassium carbonate (20.7 g, 0.15 mol) was stirred at 70° C. overnight. The mixture was evaporated in vacuo, water was added to the residue and the mixture was then extracted with dichloromethane (2×300 mL), the combined organic layers were washed with saturated sodium chloride (300 mL), dried and concentrated. Purification by flash column chromatography (silica gel, methylene chloride) provided 15.0 g of the title compound as an orange solid. $^1$H NMR (DMSO-d$_6$): δ 7.60 (dd, 1H); 7.11 (dd, 1H); 7.05 (s, 2H); 6.60 (dd, 1H); 4.40 (dd, 1H); 3.93 (dd, 1H); 3.42 (m, 1H); 2.87 (dd, 1H); 2.75 (dd, 1H).

Intermediate 2

(5-Nitro-3,4-dihydro-2H-benzo[1,4]oxazin-3-yl)-methanol

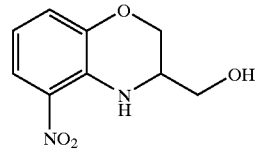

To a solution of 2-nitro-6-oxiranylmethoxy-phenylamine (14.7 g, 0.070 mol) in DMF (200 mL) was added sodium hydride (3.5 g, 60 wt. %, 0.087 mol). The resulting reaction mixture was stirred at room temperature overnight. The mixture was evaporated in vacuum, the residue diluted with water (200 mL) and extracted with methylene chloride (2×200 mL). The combined organic layers were washed with water (300 mL) and saturated sodium chloride solution (300 mL), dried (Na$_2$SO$_4$) and concentrated to provide the title compound as a dark red crystal (11.0 g). $^1$H NMR (DMSO-d$_6$): δ 8.30 (d, 1H); 7.60 (dd, 1H); 7.00 (dd, 1H); 6.65 (dd, 1H); 5.15 (t, 1H); 4.10 (m, 2H); 3.70 (m, 1H); 3.50 (m, 2H).

Intermediate 3

Toluene-4-sulfonic acid 5-nitro-3,4-dihydro-2H-benzo[1,4]oxazin-3-ylmethyl ester

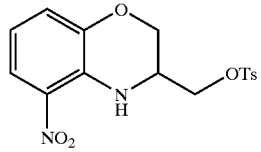

(5-Nitro-3,4-dihydro-2H-benzo[1,4]oxazin-3-yl)-methanol (6.5 g, 31.0 mmole) was dissolved in methylene chloride (200 mL), N, N-diisopropylethylamine (10.8 mL, 62 mmole) and 4-DMAP (1.18 g) were added, followed by p-toluenesulfonyl chloride (12.85 g, 67.4 mmole) and the mixture stirred at room temperature under nitrogen overnight. The mixture was diluted with methylene chloride (100 mL), washed with HCl (1N, 200 mL), saturated sodium bicarbonate (200 mL), saturated sodium chloride (200 mL) and dried (Na$_2$SO$_4$). Filtration, evaporation in vacuum and column chromatography on silica gel with 1:1 hexane/methylene chloride as eluent gave 10.5 g (93%) of the title compound as a yellow solid. $^1$H NMR (DMSO-d$_6$): δ 8.20 (d, 1H); 7.70 (d, 1H); 7.65 (dd, 1H); 7.40 (d, 2H); 7.05 (dd, 1H); 6.55 (dd, 1H); 4.10 (m, 5H); 2.40 (s, 3H).

Intermediate 4

Toluene-4-sulfonic acid 5-amino-3,4-dihydro-2H-benzo[1,4]oxazin-3-ylmethyl ester

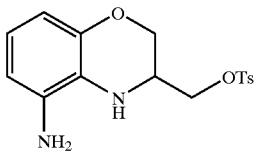

A mixture of toluene-4-sulfonic acid 5-nitro-3,4-dihydro-2H-benzo[1,4]oxazin-3-ylmethyl ester (3.64 g, 10.0 mmole), p-toluenesulfonic acid monohydrate (3.8 g, 20.0 mmole) and 0.50 g of 10% palladium on carbon in 140 mL of methanol was treated with 50 psi of hydrogen on a Parr shaker for 1 hour. The catalyst was filtered and washed with additional methanol. The solvent was evaporated in vacuum to yield 6.7 g of the p-toluenesulfonate salt of the title compound as a pink solid. This compound was used for the next step without further purification.

Intermediate 5

(2-Oxo-1,2,4,5-tetrahydroimidazo[1,5,4-de][1,4]benzoxazin-4-yl)methyl 4-methylbenzenesulfonate

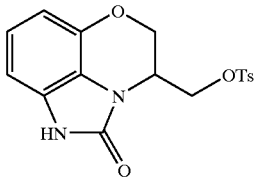

Toluene-4-sulfonic acid 5-amino-3,4-dihydro-2H-benzo[1,4]oxazin-3-ylmethyl ester (6.7 g, ~10 mmole) was dissolved in methylene chloride (100 mL), N,N-diisopropylethylamine (5.22 mL, 30.0 mmole) was added, followed by carbonyldiimidazole (4.05 g, 25.0 mmole), and the mixture was stirred at room temperature under nitrogen overnight. The mixture was diluted with methylene chloride (100 mL), washed with water (2×200 mL), saturated sodium bicarbonate (200 mL) saturated sodium chloride (200 mL) and dried ($Na_2SO_4$). Filtration, evaporation in vacuum and column chromatography on silica gel with 1% methanol/methylene chloride as eluent gave 2.0 g of the title compound as an off white solid, m.p. 140–142° C. $^1$H NMR (DMSO-$d_6$): δ 10.7 (s, 1H); 7.63 (d, 2H); 7.47 (d, 2H); 6.82 (t, 1H); 6.57 (d, 1H); 6.52 (d, 1H); 4.53 (m, 1H); 4.43 (dd, 1H); 4.34 (dd, 1H); 4.16 (dd, 1H); 4.10 (dd, 1H); 2.38 (s, 3H). MS (ESI) m/z 359 ([M−H]−).

Elemental Analysis for: $C_{17}H_{16}N_2O_5S$ Calc'd: C, 56.66; H, 4.48; N, 7.77. Found: C, 56.43; H, 4.33; N, 7.67.

EXAMPLE 1

4-{[4-(1H-indol-3-yl)-3,6-dihydropyridin-1(2H)-yl]methyl}-4,5-dihydroimidazo[1,5,4-de][1,4]benzoxazin-2(1H)-one

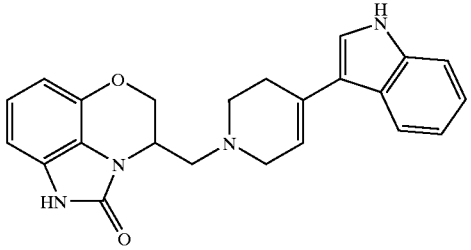

(2-Oxo-1,2,4,5-tetrahydroimidazo[1,5,4-de][1,4]benzoxazin-4-yl)methyl 4-methyl benzenesulfonate (0.50 g, 1.39 mmole) and 3-(1,2,3,6-tetrahydro-pyridin-4-yl)-1H-indole (0.82 g, 4.16 mmole) were combined in 5 mL of DMSO under nitrogen. This solution was heated to 85° C. under nitrogen for 5 hours. After completion, the reaction mixture was cooled to room temperature and partitioned between 400 mL each of ethyl acetate and water. The organic phase was washed with 250 mL portions of water and brine, dried over sodium sulfate, filtered and concentrated in vacuum. The resulting crude oil was column chromatographed on silica gel using first methylene chloride to remove impurities and then 2% methanol/methylene chloride to elute the title compound (0.40 g, m.p. 147–149° C.). $^1$H NMR (DMSO-$d_6$): δ 11.1 (s, 1H); 10.7 (s, 1H); 7.80 (d, 1H); 7.38 (d, 2H); 7.10 (t, 1H); 7.00 (t, 1H); 6.84 (t, 1H); 6.58 (dd, 2H); 6.10 (s, 1H); 4.60 (d, 1H); 4.50 (t, 1H); 4.10 (dd, 1H); 3.25 (dd, 2H); 2.78 (t, 2H); 2.64 (dd, 2H); 2.58 (dd, 2H). MS (ESI) m/z 385 ([M−H]−).

Elemental Analysis for: $C_{23}H_{22}N_4O_2$.0.32 $CH_2Cl_2$ Calc'd: C, 67.72; H, 5.52; N, 13.54. Found: C, 68.02; H, 5.80; N, 13.18.

EXAMPLE 2

4-{[4-(5-Fluoro-1H-indol-3-yl)-3,6-dihydropyridin-1(2H)-yl]methyl}-4,5-dihydroimidazo]1,5,4-de][1,4]benzoxazin-2(1H)-one

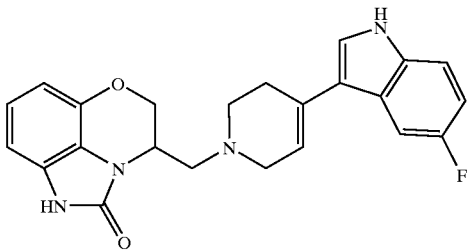

(2-Oxo-1,2,4,5-tetrahydroimidazo[1,5,4-de][1,4]benzoxazin-4-yl)methyl 4-methylbenzenesulfonate (0.40 g, 1.1 mmole) and 5-fluoro-3-(1,2,3,6-tetrahydro-pyridin-4-yl)-1H-indole (0.72 g, 3.33 mmole) were combined in 5 mL of DMSO under nitrogen. This solution was heated to 85° C. under nitrogen for 5 hours. After completion, the reaction was cooled to room temperature and partitioned between 400 mL each of ethyl acetate and water. The organic phase was washed with 250 mL of water and brine, dried over sodium sulfate, filtered and concentrated in vacuum. The crude oil was column chromatographed on silica gel using first methylene chloride to remove impurities and then 2% methanol/methylene chloride to elute the title compound (0.255 g, m.p. 152–155° C.). $^1$H NMR (DMSO-$d_6$): δ 11.0 (s, 1H); 10.7 (s, 1H); 7.53 (dd, 1H); 7.47 (d, 1H); 7.35 (dd, 1H); 6.95 (t, 1H); 6.84 (t, 1H); 6.58 (dd, 2H); 6.05 (s, 1H); 4.60 (d, 1H); 4.50 (t, 1H); 4.10 (dd, 1H); 3.25 (dd, 2H); 2.78 (t, 2H); 2.64 (dd, 2H); 2.58 (dd, 2H). MS (ESI) m/z 405 ([M+H]+).

Elemental Analysis for: $C_{23}H_2,FN_4O_2$.0.13 $CH_2Cl_2$ Calc'd: C, 66.87; H, 5.16; N, 13.48. Found: C, 66.87; H, 5.33; N, 13.31.

EXAMPLE 3

4-{[4-(5-chloro-1H-indol-3-yl)-3,6-dihydropyridin-1(2H)-yl]methyl}-4,5-dihydroimidazo[1,5,4-de][1,4]benzoxazin-2(1H)-one

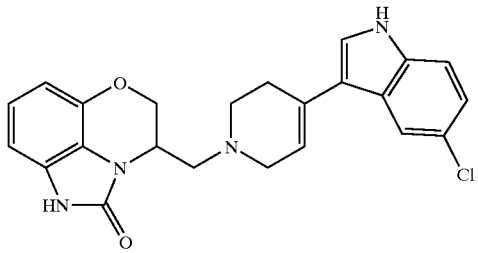

(2-Oxo-1,2,4,5-tetrahydroimidazo[1,5,4-de][1,4]benzoxazin-4-yl)methyl 4-methylbenzenesulfonate (0.40 g, 1.1 mmole) and 5-chloro-3-(1,2,3,6-tetrahydro-pyridin-4-yl)-1 H-indole (0.70 g, 2.99 mmole) were combined in 5 mL of DMSO under nitrogen. This solution was heated to 85° C. under nitrogen for 5 hours. After completion, the reaction was cooled to room temperature and partitioned between 400 mL each of ethyl acetate and water. The organic phase was washed with 250 mL of water and brine, dried over sodium sulfate, filtered and concentrated in vacuum. The resulting crude oil was column chromatographed on silica gel using first methylene chloride to remove impurities and then 2% methanol/methylene chloride to elute the title compound (0.234 g, m.p. 153–155° C). $^1$H NMR (DMSO-$d_6$): δ 11.0 (s, 1H); 10.7 (s, 1H); 7.78 (d, 1H); 7.47 (d, 1H); 7.38 (dd, 1H); 7.10 (dd, 1H); 6.84 (t, 1H); 6.58 (dd, 2H); 6.05 (s, 1H); 4.60 (d, 1H); 4.50 (t, 1H); 4.10 (dd, 1H); 3.25 (dd, 2H); 2.78 (t, 2H); 2.64 (dd, 2H); 2.58 (dd, 2H). MS (ESI) m/z 421 ([M+H]+).

Elemental Analysis for: $C_{23}H_{21}ClN_4O_2$.0.14 $CH_2Cl_2$ Calc'd: C, 64.22; H, 4.96; N, 12.95. Found: C, 64.18; H, 5.05; N, 12.81.

EXAMPLE 4

3-{1-[(2-Oxo-1,2,4,5-tetrahydroimidazo[1,5,4-de][1,4]benzoxazin-4-yl)methyl]-1,2,3,6-tetrahydropyridin-4-yl}-1H-indole-5-carbonitrile

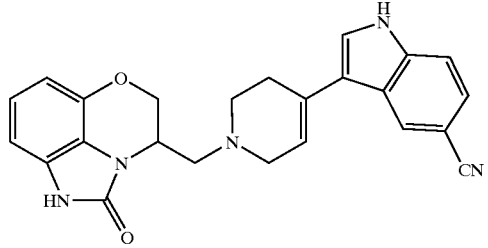

(2-Oxo-1,2,4,5-tetrahydroimidazo[1,5,4-de][1,4]benzoxazin-4-yl)methyl 4-methyl benzenesulfonate (0.30 g, 0.83 mmole) and 5-cyano-3-(1,2,3,6-tetrahydro-pyridin-4-yl)-1H-indole (0.65 g, 2.93 mmole) were combined in 3.5 mL of DMSO under nitrogen. This solution was heated to 85° C. under nitrogen for 5 hours. After completion, the reaction was cooled to room temperature and partitioned between 400 mL each of ethyl acetate and water. The organic phase was washed with 250 mL portions of water and brine, dried over sodium sulfate, filtered and concentrated in vacuum. The crude residue was column chromatographed on silica gel using first methylene chloride to remove impurities and then 2% methanol/methylene chloride to elute the title compound (0.127 g, m.p. >160° C.). $^1$H NMR (DMSO-$d_6$): δ 11.7 (s, 1H); 10.7 (s, 1H); 8.30 (s, 1H); 7.60 (s, 1H); 7.55 (d, 1H); 7.45 (d, 1H); 6.84 (t, 1H); 6.58 (dd, 2H); 6.20 (s, 1H); 4.60 (d, 1H); 4.50 (t, 1H); 4.10 (dd, 1H); 3.25 (dd, 2H); 2.78 (t, 2H); 2.64 (dd, 2H); 2.58 (dd, 2H). MS (ESI) m/z412 ([M+H]+).

Elemental Analysis for: $C_{24}H_{21}N_5O_2$.0.15 $C_6H_{14}$.0.13 $CH_2Cl_2$ Calc'd: C, 69.04; H, 5.41; N, 16.08. Found: C, 69.03; H, 5.55; N, 15.90.

EXAMPLE 5

4-{[4-(7-Fluoro-1H-indol-3-yl)-3,6-dihydropyridin-1(2H)-yl]methyl}-4,5-dihydroimidazo[1,5,4-de][1,4]benzoxazin-2(1H)-one

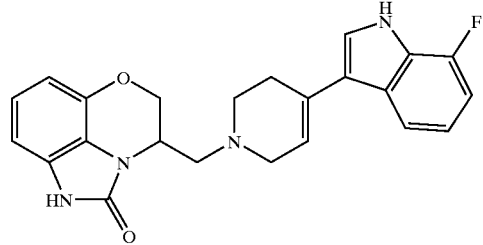

2-Oxo-1,2,4,5-tetrahydroimidazo[1,5,4-de][1,4]benzoxazin-4-yl)methyl 4-methyl benzenesulfonate (0.30 g, 0.83 mmole) and 7-fluoro-3-(1,2,3,6-tetrahydro-pyridin-4-yl)-1H-indole (0.65 g, 3.01 mmole) are combined in 3.5 mL of DMSO under nitrogen. This solution was heated to 85° C. under nitrogen for 5 hours. After completion, the reaction was cooled to room temperature and partitioned between 400 mL each of ethyl acetate and water. The organic phase was washed with 250 mL portions of water and brine, dried over sodium sulfate, filtered and concentrated in vacuum.

The crude residue was column chromatographed on silica gel using first methylene chloride to remove impurities and then 2% methanol/methylene chloride to elute the title compound (0.173 9, m.p. >120° C.). $^1$H NMR (DMSO-d$_6$): δ 11.6 (s, 1H); 10.7 (s, 1H); 7.62 (d, 1H); 7.43 (s, 1H); 7.00 (m, 1H); 6.95 (m, 1H); 6.84 (t, 1H); 6.58 (dd, 2H); 6.12 (s, 1H); 4.60 (d, 1H); 4.50 (t, 1H); 4.10 (dd, 1H); 4.02 (dd, 1H); 3.25 (dd, 2H); 2.78 (t, 2H); 2.64 (dd, 2H); 2.58 (dd, 2H). MS (ESI) m/z 405 ([M+H]+).

Elemental Analysis for: C$_{23}$H$_{21}$FN$_4$O$_2$0.0.55 C$_4$H$_8$O$_2$ Calc'd: C, 66.83; H, 5.65; N, 12.37. Found: C, 66.82; H, 5.77; N, 12.36.

Intermediate 6

(5-Amino-3,4-dihydro-2H-benzo[1,4]oxazin-3-yl)-methanol

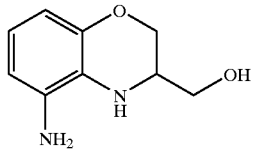

A mixture of 5-nitro-3,4-dihydro-2H-benzo[1,4]oxazin-3-yl)-methanol (10.0 g, 47.6 mmole), p-toluenesulfonic acid monohydrate (19.0 g, 0.1 mole) and 1.0 g of 10% palladium on carbon in 250 mL of methanol was treated with 50 psi of hydrogen on a Parr shaker for 2 hours. The catalyst was filtered and washed with additional methanol. The solvent was evaporated in vacuum to yield 28 g of the p-toluenesulfonate of the title compound as a pink solid. This compound was used for the next step without further purification.

Intermediate 7

(2-Methyl-3,4-dihydro-5-oxa-1,2a-diaza-acenaphthylen-3-yl)-methanol

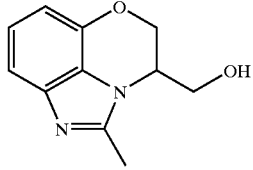

(5-Amino-3,4-dihydro-2H-benzo[1,4]oxazin-3-yl)-methanol (11.8 g, 21.0 mmole) was dissolved in acetic acid (400 mL) and the resulting mixture was stirred at 95° C. overnight. After completion, the reaction was cooled to room temperature and solvent was removed under vacuum and replaced with methanol. Potassium carbonate (2 g) was added and the mixture stirred at room temperature for 1 hour. The solvent was removed and the residue partitioned between 400 mL each of methylene chloride and saturated aqueous sodium bicarbonate. The organic phase was washed with brine, dried over sodium sulfate, filtered and concentrated in vacuum. The crude residue was column chromatographed on silica gel using first methylene chloride to remove impurities and then 5% methanol/methylene chloride to elute 2.34 g of the title compound. $^1$H NMR (DMSO-d$_6$): δ 7.10 (d, 1H); 7.00 (t, 1H); 6.60 (d, 1H); 5.30 (t, 1H); 4.60 (d, 2H); 4.10 (dd, 1H); 3.60 (m, 2H); 2.50 (s, 3H).

Intermediate 8

Toluene-4-sulfonic acid 2-methyl-3,4-dihydro-5-oxa-1,2a-diaza-acenaphthylen-3-ylmethyl ester

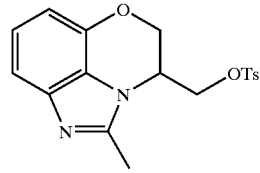

(2-Methyl-3,4-dihydro-5-oxa-1,2a-diaza-acenaphthylen-3-yl)-methanol (2.0 g, 9.8 mmole) was dissolved in pyridine (35 mL), p-toluenesulfonyl chloride (4.0 g, 20.9 mmole) was added and the resulting mixture was stirred at room temperature overnight. The solvent was removed and the residue partitioned between 400 mL each of methylene chloride and saturated aqueous sodium bicarbonate. The organic phase was washed with brine, dried over sodium sulfate, filtered and concentrated in vacuum. The crude residue was column chromatographed on silica gel using methylene chloride to elute 2.6 g of the title compound. $^1$H NMR (DMSO-d$_6$): δ 7.60 (d, 1H); 7.20 (m, 3H); 7.05 (t, 1H); 6.65 (d, 1H); 4.75 (d, 1H); 4.57 (dd, 1H); 4.10 (m, 3H); 2.58 (s, 3H); 2.47 (s, 3H).

EXAMPLE 6

4-{[4-(1H-indole-3-yl)-3,6-dihydropyridin-1(2H)-yl]methyl}-2-methyl-4,5-dihydroimidazo[1,5,4-de][1,4]benzoxazine

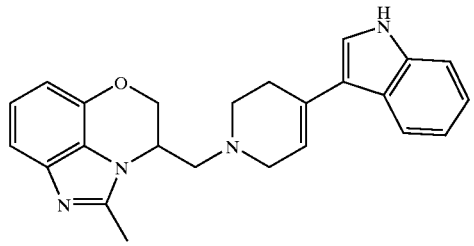

Toluene-4-sulfonic acid 2-methyl-3,4-dihydro-5-oxa-1,2a-diaza-acenaphthylen-3-ylmethyl ester (1.0 g, 2.6 mmole) and 3-(1,2,3,6-tetrahydro-pyridin-4-yl)-1H-indole (1.8 g, 9.1 mmole) were combined in 10 mL of DMSO under nitrogen. This solution was heated to 55° C. under nitrogen for 3 days. After completion, the reaction was cooled to room temperature and partitioned between 400 mL each of ethyl acetate and water. The organic phase was washed with water and brine, dried over sodium sulfate, filtered and concentrated in vacuum. The crude residue was column chromatographed on silica gel using first methylene chloride to remove impurities and then 2% methanol/methylene chloride to elute 0.182 g of the title compound, m.p. 222–225° C. $^1$H NMR (DMSO-d$_6$): δ 11.1 (s, 1 H); 7.80 (d, 1 H); 7.38 (dd, 2H); 7.10 (m, 2H); 7.00 (m, 2H); 6.64 (d, 1 H); 6.11 (s, 1H); 4.98 (t, 1H); 4.70 (d, 1H); 4.15 (dd, 1H); 3.20 (dd, 2H); 2.80 (m, 1H), 2.70 (dd, 1H); 2.65 (m, 1H); 2.58 (m, 1H); 2.57 (s, 3H); 2.54 (m, 2H). MS (ESI) m/z 383 ([M+H]+).

Elemental Analysis for: C$_{24}$H$_{24}$N$_4$O.0.07 CH$_2$Cl$_2$ Calc'd: C, 74.05; H, 6.23; N, 14.35. Found: C, 74.03; H, 6.33; N, 14.10.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of Formula I:

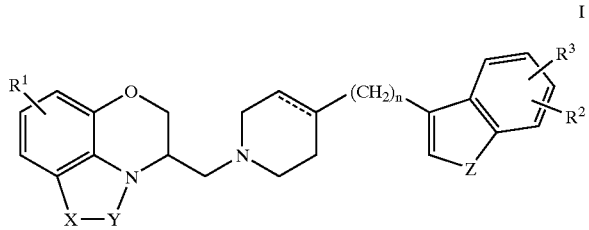

wherein

X—Y is —N=C($R^4$)—, —NH—C(O)—, —NH—C(O)—C(O)—, —NH—C(S)— or —NH—S(O)$_2$—;

Z is O, S or $NR^5$, in which $R^5$ is hydrogen or alkyl of 1 to 6 carbon atoms;

$R^1$, $R^2$ and $R^3$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyl of 2 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

$R^4$ is hydrogen, halo, amino, mono- or di-alkylamino in which each alkyl group has 1 to 6 carbon atoms or alkyl of 1 to 6 carbon atoms;

the dotted line represents an optional double bond; and n is 0, 1 or 2;

or a phannaceutically acceptable salt thereof.

2. A compound according to claim 1, wherein $R^4$ is hydrogen, amino or alkyl of 1 to 6 carbon atoms.

3. A compound according to claim 1, wherein $R^4$ is hydrogen or alkyl of 1 to 3 carbon atoms.

4. A compound according to claim 1, wherein X—Y is —NH—C(O)—.

5. A compound according to claim 1, wherein Z is $NR^5$.

6. A compound according to claim 1, wherein the dotted line is a double bond.

7. A compound according to claim 1, wherein n is 0.

8. A compound according to claim 1 having Formula Ia:

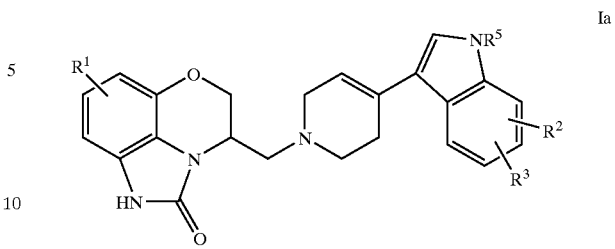

or a pharmaceutically acceptable salt thereof.

9. A compound according to claim 1, wherein $R^5$ is hydrogen or alkyl of 1 to 3 carbon atoms.

10. A compound according to claim 1, wherein $R^5$ is hydrogen or methyl.

11. A compound according to claim 1, wherein $R^1$ is hydrogen, halo, cyano, trifluoromethyl, alkyl of 1 to 6 carbon atoms or alkoxy of 1 to 6 carbon atoms.

12. A compound according to claim 1, wherein $R^1$ is hydrogen, halo or alkoxy of 1 to 6 carbon atoms.

13. A compound according to claim 1, wherein $R^1$ is hydrogen.

14. A compound according to claim 1, wherein $R^2$ and $R^3$ are independently selected from hydrogen, hydroxy, halo, cyano, carboxanildo, alkyl of 1 to 6 carbon atoms or alkoxy of 1 to 6 carbon atoms.

15. A compound according to claim 1, wherein $R^2$ and $R^3$ are independently selected from hydrogen, hydroxy, halo, cyano, carboxamido, alkyl of 1 to 6 carbon atoms, or alkoxy of 1 to 6 carbon atoms.

16. A compound according to claim 1, wherein $R^2$ and $R^3$ are independently selected from hydrogen, cyano or halogen.

17. A compound according to claim 1, wherein $R^1$ is hydrogen, halo or alkoxy of 1 to 6 carbon atoms, $R^2$ and $R^3$ are hydrogen, cyano or halogen, $R^4$ is hydrogen or alkyl of 1 to 3 carbon atoms, Z is $NR^5$ , $R^5$ is hydrogen or ailcyl of 1 to 3 carbon atoms and n is 0.

18. A compound according to claim 1, wherein said compound is 4- {[4-(1H-indol-3-yl)-3,6-dihydropyridin-1(2H)-yl]methyl)-4,5-dihydroimidazo [1,5,4-de][1,4]benzoxazin-2(1H)-one or a pharmaceutically acceptable salt thereof.

19. A compound according to claim 1, wherein said compound is 4-{[4-(5-fluoro-1H-indol-3-yl)-3,6-dihydropyridin-1(2H)-yl]methyl)-4,5-dihydroimidazo[1,5,4-de][1,4]benzoxazin-2(1H)-one or a pharmaceutically acceptable salt thereof.

20. A compound according to claim 1, wherein said compound is 4-{[4-(5-chloro-1H-indol-3-yl)-3,6-dihydropyridin-1(2H)-yl]methyl)-4,5-dihydroimidazo[1,5,4-de][1,4]benzoxazin-2(1H)-one or a pharmaceutically acceptable salt thereof.

21. A compound according to claim 1, wherein said compound is 3-{1-[(2-oxo-1,2,4,5-tetrahydroimidazo[1,5,4-de][1,4]benzoxazin-4-yl)methyl]-1,2,3,6-tetrahydropyridin-4-yl}-1H-indole-5-carbonitrile or a phannaceutically acceptable salt thereof.

22. A compound according to claim 1, wherein said compound is 4-{[4-(7-fluoro-1H-indol-3-yl)-3,6-dihydropyridin-1(2H)-yl]methyl)-4,5-dihydroimidazo[1,5,4-de][1,4]benzoxazin-2(1H)-one or a pharmaceutically acceptable salt thereof.

23. A compound according to claim 1, wherein said compound is 4-{[4-(1 H-indol-3-yl)-3,6-dihydropyridin-1

(2H)-yl]methyl}-2-methyl-4,5-dihydroimidazo[1,5,4-de][1,4]benzoxazine or a pharmaceutically acceptable salt thereof.

24. A compound according to claim 1, wherein said compound is the S enantiomer, substantially free of the R enantiomer of said compound.

25. A method of treating a subject suffering from a condition selected from depression, anxiety, panic disorder, post-traumatic stress disorder, premenstrual dysphoric disorder, attention deficit disorder, obsessive compulsive disorder, social anxiety disorder, generalized anxiety disorder, obesity, anorexia nervosa, bulimia nervosa, vasomotor flushing, cocaine and alcohol addiction, and premature ejaculation, comprising the step of:

administering to said subject suffering from said condition, a therapeutically effective amount of a compound according to claim 1 or a pharmaceutically acceptable salt thereof.

26. A method according to claim 25, wherein the condition is depression.

27. A method according to claim 25, wherein the condition is selected from the group consisting of obsessive-compulsive disorder, panic attacks, generalized anxiety disorder, and social anxiety disorder.

28. A pharmaceutical composition, comprising:

an effective amount of compound according to claim 1 or a pharmaceutically acceptable salt thereof; and a pharmaceutically acceptable carrier or excipient.

* * * * *